(12) United States Patent
Hansen et al.

(10) Patent No.: US 12,178,637 B2
(45) Date of Patent: Dec. 31, 2024

(54) IMAGE FUSION-BASED TRACKING WITHOUT A TRACKING SENSOR

(71) Applicant: B-K Medical ApS, Herlev (DK)

(72) Inventors: Jens Munk Hansen, Kobenhavn N (DK); Henrik Jensen, Nordhavn (DK); Jacob Bjerring Olesen, Copenhagen (DK); Fredrik Gran, Limhamn (SE); Bo Martins, Rodovre (DK)

(73) Assignee: BK Medical APS, Herlev (DK)

( * ) Notice: Subject to any disclaimer, the term of this patent is extended or adjusted under 35 U.S.C. 154(b) by 534 days.

(21) Appl. No.: 17/024,954

(22) Filed: Sep. 18, 2020

(65) Prior Publication Data

US 2022/0087638 A1    Mar. 24, 2022

(51) Int. Cl.
| | |
|---|---|
| *A61B 8/08* | (2006.01) |
| *G01S 7/52* | (2006.01) |
| *G01S 15/89* | (2006.01) |
| *A61B 5/00* | (2006.01) |

(52) U.S. Cl.
CPC .......... *A61B 8/0841* (2013.01); *A61B 8/5207* (2013.01); *G01S 7/52026* (2013.01); *G01S 15/89* (2013.01); *A61B 5/4381* (2013.01)

(58) Field of Classification Search
CPC . A61B 8/0841; A61B 8/5207; G01S 7/52026; G01S 15/89
See application file for complete search history.

(56) References Cited

U.S. PATENT DOCUMENTS

| | | | | |
|---|---|---|---|---|
| 7,438,685 | B2 * | 10/2008 | Burdette | A61B 6/5247 |
| | | | | 600/439 |
| 9,165,362 | B2 | 10/2015 | Siewerdsen et al. | |
| 10,130,330 | B2 | 11/2018 | Vignon et al. | |
| 11,540,811 | B2 * | 1/2023 | Dufour | A61B 8/4416 |

(Continued)

FOREIGN PATENT DOCUMENTS

DE    102014212089 A1 *  7/2015  ............. A61B 34/10

OTHER PUBLICATIONS

BK Medical, Clinically Significant Answers from (bkFusion) Prostate Biopsies. Downloaded on Jul. 15, 2020 from BK Medical.

(Continued)

*Primary Examiner* — Amal Aly Farag
(74) *Attorney, Agent, or Firm* — Daugherty & Del Zoppo, COo, LPA

(57) ABSTRACT

An ultrasound imaging system include a console with transmit circuitry configured to generate an excitation electrical pulse that excites transducer elements of a probe to produce an ultrasound pressure field and configured to receive an echo signal generated in response to the ultrasound pressure field interacting with tissue. The console further includes receive circuitry configured to convert the echo signal into an electrical signal, and an echo processor configured to generate a live ultrasound image based on the electrical signal into. The console further includes a tracking processor configured to extract, in real-time, a feature common to both the live ultrasound image and previously generated volumetric image data from at least the live ultrasound image, and register, in real-time, the live ultrasound image with previously generated volumetric image data based on the common feature extracted in real-time to create the fused image. A display displays the fused image.

19 Claims, 2 Drawing Sheets

(56) References Cited

U.S. PATENT DOCUMENTS

| | | | |
|---|---|---|---|
| 2010/0061601 A1* | 3/2010 | Abramoff | G06T 7/33 |
| | | | 382/117 |
| 2011/0178389 A1 | 7/2011 | Kumar et al. | |
| 2015/0086956 A1 | 3/2015 | Savitsky et al. | |
| 2016/0317119 A1* | 11/2016 | Tahmasebi Maraghoosh | |
| | | | A61B 8/467 |
| 2017/0176565 A1* | 6/2017 | Kwak | A61B 5/4381 |
| 2018/0008237 A1* | 1/2018 | Venkataraman | A61B 8/4263 |
| 2018/0360413 A1* | 12/2018 | De Wijs | A61B 8/0841 |
| 2019/0365355 A1* | 12/2019 | Eldar | A61B 8/488 |
| 2020/0008779 A1* | 1/2020 | Göksel | G01S 7/52036 |
| 2020/0345426 A1* | 11/2020 | Glossop | A61B 8/0841 |
| 2021/0045715 A1* | 2/2021 | Mauldin | A61N 7/02 |

OTHER PUBLICATIONS

Philips, Auto Registration on EPIQ Evolution 1.0. Downloaded on Jul. 15, 2020 from Philips Ultrasound.
BK Medical, Setting up and Using bkFusion on the bk3000 & 500 Systems—Transrectal, User Guide, Jan. 2020.

\* cited by examiner

IMAGE FUSION-BASED TRACKING WITHOUT A TRACKING SENSOR

TECHNICAL FIELD

The following generally relates to ultrasound and more particularly to fusing a live ultrasound image with previously generated volumetric image data to spatial track an ultrasound probe with respect to the previously generated volumetric image data without information from a tracking sensor affixed to the probe.

BACKGROUND

Ultrasound imaging has provided useful information about the interior characteristics of an object or subject under examination. For example, ultrasound-guided prostate biopsy has been used to assist with advancing a biopsy needle to and removing a tissue sample(s) from a suspect area of the prostate, e.g., to rule out/diagnose cancer.

Without a tracking sensor to track a position of the probe, a clinician needs to mentally register a live ultrasound image, which includes the biopsy needle, with previously generated volumetric data such as computed tomography (CT), magnetic resonance (MR), and/or other volumetric image data. Unfortunately, this mental registration has been quite difficult and is further complicated by the fact that it is often not possible to scan the patient with orthogonal, sagittal or coronal planes, which are the views used for interpretation of CT or MR images.

With a tracking sensor to track the position of the probe, a tracking system can be programmed to fuse the live ultrasound image with the previously generated volumetric data based on the sensor signal, which provide a relative position of the probe with respect to the previously generated volumetric data. The clinician can then use the fused live ultrasound/previously generated volumetric data to guide the biopsy needle to the target tissue. Unfortunately, this requires one or more sensors to be affixed to the probe and additional hardware and/or software, which increase overall complexity and cost of the ultrasound system.

In view of at least the foregoing, the is an unresolved need for another ultrasound image fusion.

SUMMARY

Aspects of the application address the above matters, and others.

In one aspect, an ultrasound imaging system include a console with transmit circuitry configured to generate an excitation electrical pulse that excites transducer elements of a probe to produce an ultrasound pressure field and configured to receive an echo signal generated in response to the ultrasound pressure field interacting with tissue. The console further includes receive circuitry configured to convert the echo signal into an electrical signal. The console further includes an echo processor configured to generate a live ultrasound image each frame based on the electrical signal into. The console further includes a tracking processor configured to extract, in real-time, a feature common to both the live ultrasound image and previously generated volumetric image data from at least the live ultrasound image, and register, in real-time, the live ultrasound image with previously generated volumetric image data based on the common feature extracted in real-time to create the fused image. The console further includes a display configured to display the fused image.

In another aspect, yet another aspect, a method includes receiving a live ultrasound image. The method further includes extracting, in real-time, a feature common to both the live ultrasound image and previously acquired pre-procedure volumetric image data from at least the live ultrasound image. The method further includes registering, in real-time, the live ultrasound image with the previously acquired pre-procedure volumetric image data based on the extracted feature, thereby generating a fused image. The method further includes displaying the fused image.

In yet another aspect, a computer readable medium encoded with computer readable instructions that when executed by a processor cause the processor to: receive an initial live ultrasound image, register the initial live ultrasound image with the previously acquired pre-procedure volumetric image data based on a user input, and generate initial parameters of the image transformation.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following describes an image fusion-based tracking approach that does not require a tracking sensor affixed to an ultrasound probe to provide a position of the ultrasound probe with respect to previously generated volumetric image data of a subject under examination. As described in greater detail below, in one instance this is achieved by performing real-time image segmentation of at least a live ultrasound image and registration of the live ultrasound image with the previously generated volumetric image data, which is used to track the ultrasound probe.

Figure 1:
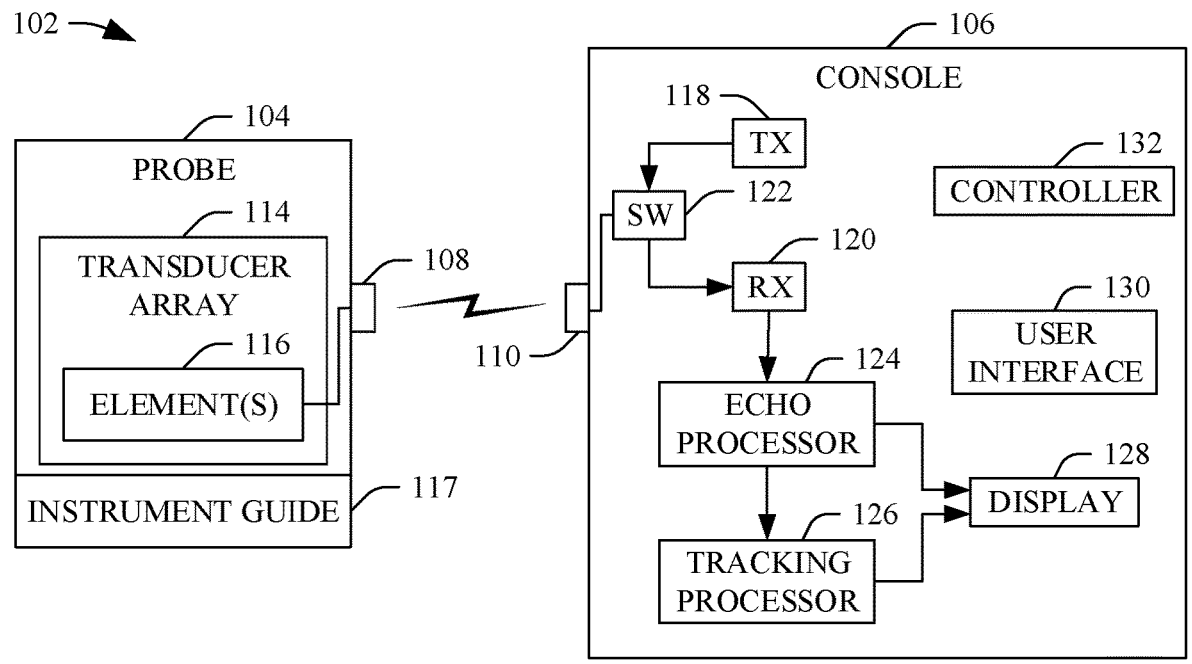
FIG. 1 illustrates an example imaging system, in accordance with an embodiment(s) herein.

FIG. 1 illustrates an example imaging system 102 such as an ultrasound imaging system/scanner. The imaging system 102 includes a probe 104 and a console 106, which interface with each other through suitable complementary wireless interfaces 108 and 110 and/or hardware (e.g., complementary cable connectors and a cable, etc.).

The probe 104 includes a transducer array 114 with one or more transducer elements 116. The probe 104 is configured for 1-D, 2-D, 3-D and/or 4-D imaging. The transducer elements 116 include a 1-D or 2-D, linear, curved and/or otherwise shaped, fully populated or sparse, etc. single or multiple arrays (e.g., biplane, sagittal and transverse, etc.). The transducer elements 116 are configured to convert an excitation electrical pulse into an ultrasound pressure field and convert a received ultrasound pressure field (an echo) into electrical (e.g., a radio frequency (RF)) signal. In one instance, for 3-D and/or 4-D imaging, the transducer array is swept or rotated to acquire volumetric data using mechanical and/or electronic approaches. Mechanical approaches include tilting the transducer via a motor inside the probe and/or otherwise. Electronic approaches include electronically steering the emitted ultrasound beam.

In the illustrated example, the probe 104 further includes an instrument guide 117 removably coupled to the probe 104 and configured to guide one or more instruments such as a biopsy needle and/or other instrument. In one instance, the probe 104 is a 3-D ultrasound endocavity probe with a rotating transducer array, wherein the drive system that rotates the transducer array is inside of an elongate shaft and offset from a center-line of the shaft and does not physically interfere with advancement of the biopsy needle in the instrument guide 117 along the center-line and sagittal plane of the shaft and in-plane with a sagittal scan plane of a transducer array 114. An example of such a probe is described in PD09016, application Ser. No. 17/025,394, entitled "3-D Endocavity Ultrasound Probe with a Needle Guide," filed on Sep. 18, 2020, and assigned to BK Medical ApS, which is incorporated herein by reference in its entirety. In a variation, the instrument guide 117 is omitted.

The console 106 includes transmit circuitry (TX) 118 configured to generate the excitation electrical pulses and receive circuitry (RX) 120 configured to process the RF signals, e.g., amplify, digitize, and/or otherwise process the RF signals. The console 106 further includes a switch (SW) 122 configured to switch between the transmit circuitry 118 and the receive circuitry 120 for transmit and receive operations, e.g., by electrically connecting and electrically disconnecting the transmit circuitry 118 and the receive circuitry 120. In another instance, different switches are used for the transmit circuitry 118 and the receive circuitry 120.

The console 106 further includes an echo processor 124 configured to process the signal from the receive circuitry 120. For example, in one instance the echo processor 124 is configured to beamform (e.g., delay-and-sum) the signal to construct a scanplane of scanlines of data, which represents a live (2-D or 3-D) ultrasound image in the sense that it is generated based on the currently received echoes and the present location of the probe 104 with respect to the subject and is not a previously generated image. The echo processor 124 can be implemented by a hardware processor such as a central processing unit (CPU), a graphics processing unit (GPU), a microprocessor, etc.

The console 106 further includes a tracking processor 126. The tracking processor 126 is configured to fuse the live ultrasound image with previously generated volumetric image data (e.g., MR, CT, US, etc.). As described in greater detail below, in one instance this includes extracting features visible in both the live image and the previously generated volumetric image data and, after an initial alignment, performing real-time feature extraction of a current live (2-D or 3-D) image and real-time registration of the current live image with the previously generated volumetric image data based on the extracted features. In one instance, this approach provides what has been provided by an optical and/or electromagnetic tracking system, without an optical and/or electromagnetic sensor.

The console 106 further includes a display 128. The output of the echo processor 124 and/or the tracking processor 126 is scan converted to the coordinate system of the display 128 and displayed as images via the display 128.

The console 106 further includes a user interface 130, which includes one or more input devices (e.g., a button, a touch pad, a touch screen, etc.) and one or more output devices (e.g., a display screen, a speaker, etc.). The user interface 130, in one instance, allows a user to manipulate a displayed image, e.g., translate, rotate, scale, etc., during an initial registration live ultrasound image and the previously generated volumetric image data, and/or otherwise.

The console 106 further includes a controller 132 configured to control one or more of the transmit circuitry 118, the receive circuitry 120, the switch 122, the echo processor 124, the tracking processor 126, the display 128, the user interface 130, and/or one or more other components of the imaging system 102. The controller 132 can be implemented by a hardware processor such as a CPU, a GPU, a microprocessor, etc.

Figure 2:
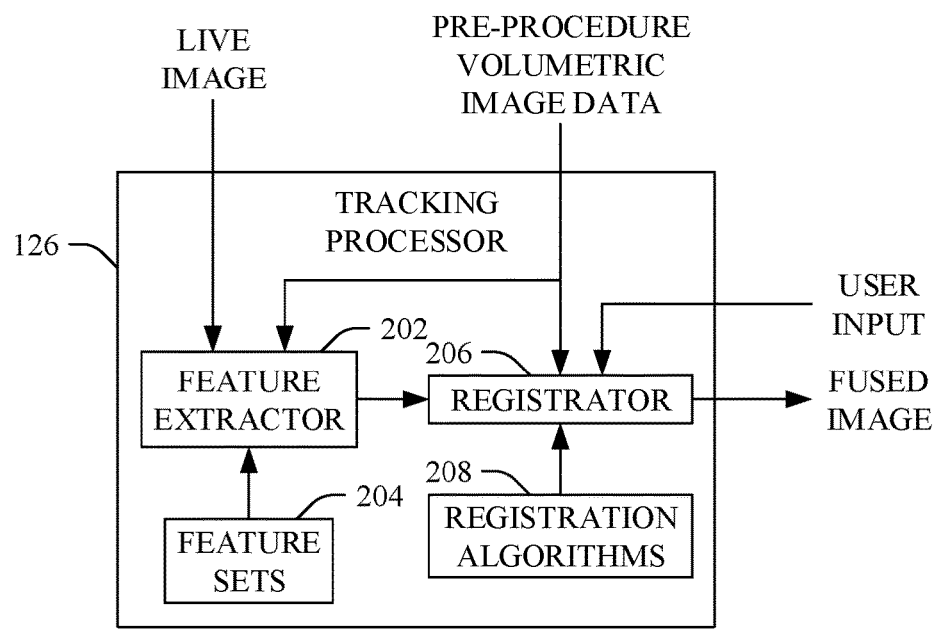
FIG. 2 illustrates an example tracking sensor of the example imaging system of FIG. 1, in accordance with an embodiment(s) herein.

FIG. 2 illustrates an example of the tracking processor 126, in accordance with an embodiment(s) herein. The illustrated tracking processor 126 receives, as an input, the pre-operative volumetric image data. The tracking processor 126 also receives, as an input, the current live image, the previously generated volumetric image data, user input for the initial registration of an initial current live image and the previously generated volumetric image data, and outputs a fused image, which can be displayed via the display 128.

The illustrated tracking processor 126 includes a feature extractor 202. The feature extractor 202 extracts features based on a set(s) of predetermined features 204. For example, the set(s) of predetermined features 204 for a prostate, liver, etc. examination would include a set of features known to be in and/or around the prostate (e.g., the urethra tree, a surface of the prostate, etc.), liver (e.g., a vascular tree, etc.), etc. The set may include a single feature and/or multiple different features. The feature extractor 202 extracts the features in the live image when the live image is received, i.e. in real-time.

With respect to vessels, in one instance the extraction includes extracting contours and/or centerlines of the vessels. By way of example, extraction of vessel boundaries can be performed by seeding a region-growing algorithm using a combination of ultrasound imaging data and velocity flow imaging (VFI) data. Examples of such an algorithm is discussed in Moshavegh et al., "Hybrid Segmentation of Vessels and Automated Flow Measures in In-Vivo Ultrasound Imaging," 2016 IEEE International Ultrasonics Symposium (IUS), and U.S. Pat. No. 10,456,113 B2, to Moshavegh et al., entitled "Wall-to-wall vessel segmentation in US imaging using a combination of VFI data and US imaging data," and filed on Sep. 8, 2016, which is incorporated herein in its entirety by reference. An un-supervised region growing approach for extracting, e.g., vessels from a 3D CT volume is described in Adams et al., "Seeded region growing," IEEE Transactions on pattern analysis and machine intelligence, Vol. 16, NO. 6, pp. 641-647, 1994.

The tracking processor 126 includes a registrator 206. The registrator 206 registers the live image and the previously generated volumetric image data based on a registration algorithm(s) 208 and the extracted features. For explanatory purposes and sake of brevity, the following describes an example using a point set registration algorithm, e.g., 2-D and/or 3-D landmark, in general. Other algorithms are contemplated herein.

Examples of suitable point set registration algorithms include correspondence-based algorithms such as outlier-free, robust registrations (maximum consensus, outlier removal, M-estimation, graduated non-convexity, certifiably robust registration, etc.), etc., and simultaneous pose and correspondence algorithms such as iterative closest point, robust point matching (e.g., thin plate spline robust point matching, etc.), kernel correlation (e.g., Gaussian mixture model, etc.), coherent point drift, sorting the correspondence space, and Bayesian coherent point drift, as well as other registration algorithms.

For the initial registration, the live image and the previously generated volumetric image data are displayed, via the display 128, superimposed, with the extracted features visually highlighted, e.g., outlined, colored, etc. For 2-D, a reference slice of the volumetric image data is displayed. In general, a reference slice is a slice where the features are easily recognizable, e.g., a bifurcation in the vessel tree or the slice where the urethra is visible. The clinician aligns the live image and the previously generated volumetric image data via an input from the user interface 130. For example, the clinician visually observes the two images and translates, rotates, scales and/or otherwise manipulates the live image until the extracted corresponding features in the two images align with each other. Once aligned, the clinician accepts the registration, and the registrator 206 initializes image transformation parameters, which represent an orientation and a location of the live image relative to a fixed coordinate system of the previously generated volumetric image data. Automated approaches are also contemplated herein.

During an image-guided procedure, the probe 104 is moved and when a current live image is received, the feature extractor 202 extracts the features from the newly received live image, and the registrator 206 registers the newly received live image and the previously generated volumetric image data based on the extracted features. In one non-limiting instance, the registration is performed by formulating a cost function, which depends on locations of the features embedded in the live image and the 3-D locations of the features extracted from previously generated volumetric image data, and updating the image transformation parameters using a numerical optimization algorithm.

In one instance, the optimization is performed using an iteration of an iterative closest point algorithm. This can be repeated until stopping criteria is satisfied, e.g., until a similarly metric has reached a local or global maximum, a predetermined maximum number of iterations has been reached, a predetermined time duration has lapsed, etc. A result is a set of image transformation parameters representing the transformation from the previous orientation and location to a new location and orientation, where the features match those from the input pre-procedure volumetric image data. In a variation, this is also performed for the initial image, which, in one instance, improves the initial image transformation parameters.

In one instance, the above is performed for each newly received live image, which forms a continuous set of image transformation parameters. In another instance, the above is performed every other frame, every third frame, . . . , every tenth frame, etc. In another instance, the above is performed with a sufficient rate for capturing the motion from frame to frame, e.g., at a rate of about 5 Hertz (Hz) to 20 Hz, such as 10 Hz (i.e. 10 times per second). In one instance, the updated parameters represent a change in a position of the probe 104 from a previous position of the probe 104. In another instance, the updated parameters represent an absolute position of the probe 104.

In an extension to the tracking described herein, prior to an intervention, where tracking is desired, a live 2D/3D image is registered to one or more 3D volumes, which in turn are registered to another 3D volume, which is the volume of interest. The one or more pre-operative volumes can be generated by a same or different modalities and registered using algorithms ranging from simple landmark registration to more advanced registration algorithms using a combinations of segmentation and a registration algorithm. An example algorithm is described in US 2020/0093464 A1 to Martins et al., entitled "Ultrasound Three-Dimensional Segmentation," and filed Sep. 24, 2018, the entirety of which is incorporated by reference herein. This extension, in one instance, improves the tracking described herein.

In another embodiment of the invention, the registration can be used to improve a different positioning system, including an optical or electromagnetic tracker. For example, where images of different modalities are acquired using different positioning of the patient and the organs are mobilized and deformed such that it is not possible to perform the ideal rigid registration, the registration, using the approach described herein, can be dynamically updated based on feature visible in the current live image.

Variations are discussed below.

In a variation, the tracking described herein can be improved by updating image transformation parameters based on a latest and an earlier results from the registration. In one instance, this includes removing outliers. An example of an outlier includes a transformation parameter that indicates a movement that is not reasonable, given the procedure. This may include applying a filter(s) to provide smooth continuous image transformation parameters as a function of time. In one example, this includes using Kalman Filter. An example of a suitable Kalman filter is discussed in Kalman et al., "A New Approach to Linear Filtering and Prediction Problems," Transactions of the ASME—Journal of Basic Engineering, 1960.

In another variation, a validity check is performed on the estimates, which can be derived from the output of the Kalman filter (the residuals) and a value of a distance function used for the registration. The validity can be used to determine whether the tracking is valid, or the clinician needs to perform a new initialization. The distance function is a measure of how good the registration is, and the residuals from the Kalman filter are a measure of how well the latest transformation matrix fits the prediction.

In another variation, additional inputs from an accelerometer and/or gyro are utilized for estimating the image transformation parameters to seed the process of registration from frame to frame. If the clinician has rotated the probe very rapidly, the features visible in the live image may be located very far from the features of the previous frame. Known fast numerical algorithms for feature registration are sufficient to find a nearest local minima and therefore seeding may help finding the correct minima and hence the correct image transformation parameters.

In another variation, the system 102 is used in conjunction with a positioning system, e.g., an optical or electromagnetic tracker. In this instance, the registration described herein can be used to adjust the positioning system. For example, where clinician believes the positioning system is incorrect, the clinician can invoke the tracker processor 126 to re-align the fused images.

Figure 3:
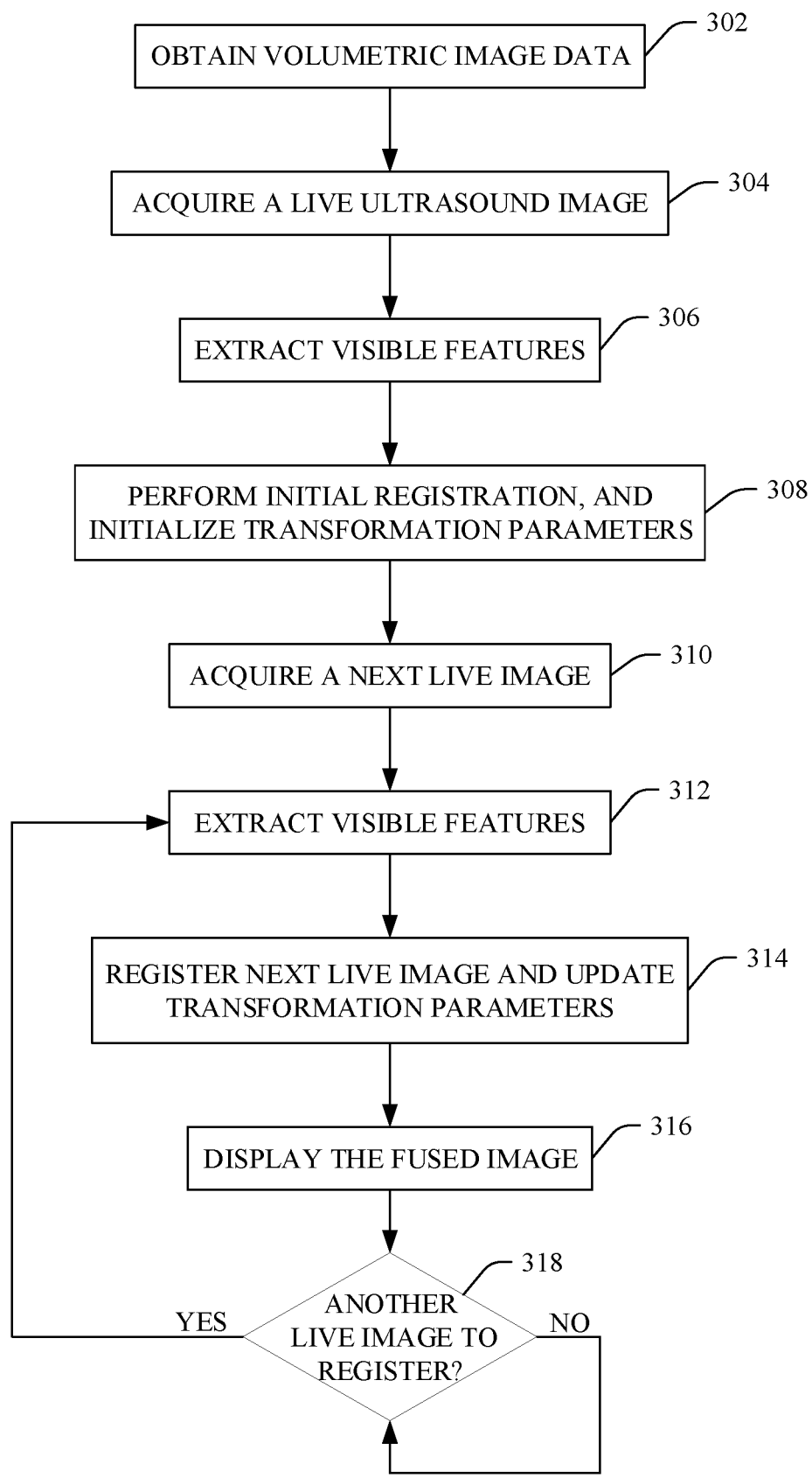
FIG. 3 illustrates an example method, in accordance with an embodiment(s) herein.

FIG. 3 illustrates a method, in accordance with an embodiment(s) herein.

At 302, previously generated volumetric image data of a subject under examination is obtained, as described herein and/or otherwise.

At 304, a live (2-D or 3-D) ultrasound image is obtained, as described herein and/or otherwise.

At 306, features visible in the live image and the previously generated volumetric image data are extracted in real-time from at least the live image, as described herein and/or otherwise.

At 308, the live image is initially registered, based on user input, with a reference slice of the previously generated volumetric image data, which initializes parameters of an image transformation, as described herein and/or otherwise.

At 310, a next live image is acquired, as described herein and/or otherwise.

At 312, features visible in the next live are extracted in real-time, as described herein and/or otherwise.

At 314, the next live image is registered, in real-time, with the previously generated volumetric image data, which updates the parameters of the image transformation, as described herein and/or otherwise.

At 316, the fused image is displayed, as described herein and/or otherwise.

At 318, if another live image to register is available, acts 310-316 are repeated for that live image, as described herein and/or otherwise.

The above may be implemented at least in part by way of computer readable instructions, encoded or embedded on computer readable storage medium (which excludes transitory medium), which, when executed by a computer processor(s) (e.g., central processing unit (CPU), microprocessor, etc.), cause the processor(s) to carry out acts described herein. Additionally, or alternatively, at least one of the computer readable instructions is carried by a signal, carrier wave or other transitory medium (which is not computer readable storage medium).

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
    a console, including:
        transmit circuitry configured to generate an excitation electrical pulse that excites transducer elements of a probe to produce an ultrasound pressure field and configured to receive an echo signal generated in response to the ultrasound pressure field interacting with tissue;
        receive circuitry configured to convert the echo signal into an electrical signal;
        an echo processor configured to generate a live ultrasound image each frame based on the electrical signal;
        a tracking processor configured to:
            obtain the live ultrasound image and volumetric image data that was previously generated by another imaging system, which was configured for three-dimensional imaging;
            extract, in real-time, an anatomical feature common to both the live ultrasound image and the previously generated volumetric image data from at least the live ultrasound image; and
            register, in real-time, the live ultrasound image with the volumetric image data based on the common anatomical feature extracted in real-time to create a fused image;
            wherein the tracking processor registers the live ultrasound image with the volumetric image data based on image registration transformation parameters, updates the image registration transformation parameters based on a latest result of the registration and an earlier result of the registration and applies a filter removing movement outliers;
        and a display configured to display the fused image.
2. The ultrasound imaging system of claim 1, wherein the tracking processor fuses the live image and the previously generated volumetric image data without information from a positioning system to provide a relative position between the live image and the volumetric image data.
3. The ultrasound imaging system of claim 1, wherein the tracking processor continually fuses, in real-time, newly generated live ultrasound images with the volumetric image data, thereby continually creating updated fused images.
4. The ultrasound imaging system of claim 3, wherein the tracking processor continually fuses only a predetermined sub-set of the newly generated live ultrasound images.
5. The ultrasound imaging system of claim 4, wherein the tracking processor spatially tracks a biopsy instrument during an ultrasound-guided transrectal prostrate biopsy procedure performed with the ultrasound imaging system based on the fused images.
6. The ultrasound imaging system of claim 1, wherein the tracking processor, prior to receiving the live ultrasound image: receives an initial live ultrasound image, extracts, in real-time, the common feature from an initial live ultrasound image, registers the initial live ultrasound image with the volumetric image data based on the common feature extracted, and initializes parameters of an image transformation.
7. The ultrasound imaging system of claim 6, wherein the tracking processor updates the parameters of the image transformation after each new registration.
8. The ultrasound imaging system of claim 1, wherein the live ultrasound image is a two-dimensional image or a three-dimensional image.
9. The ultrasound imaging system of claim 1, wherein the registration is dynamically updated based on a feature visible in the live ultrasound image.
10. The ultrasound imaging system of claim 1, further comprising: a positioning system for providing a relative position between a first live image and the volumetric image data.
11. The ultrasound imaging system of claim 10, wherein the first live ultrasound image is registered and fused with the volumetric image data and the registration of the first live ultrasound image and the volumetric image is adjusted to re-align the fused images based on an extracted feature that is common to both the first live ultrasound image and the volumetric image data.
12. The ultrasound imaging system of claim 10, wherein the console receives a user input indicating the registration and fusing of the first live ultrasound image and the previously generated volumetric image data that are based on the relative position provided by the positioning system is incorrect, and the input invokes the tracking processor to perform the re-alignment of the fused images.
13. The ultrasound imaging system of claim 1, wherein the tracking processor is configured to perform the registration by formulating a cost function.
14. The ultrasound imaging system of claim 13, wherein the cost function depends on a location of the common feature in the live ultrasound image and the volumetric image data.
15. The ultrasound imaging system of claim 13, wherein the cost function includes a numerical optimization algorithm.
16. The ultrasound imaging system of claim 6, wherein the tracking processor validates the registration.
17. The ultrasound imaging system of claim 16, wherein the tracking processor validates the registration based on a value of a distance function for the registration.

18. The ultrasound imaging system of claim 1, wherein the anatomical feature is at least one of in and around the anatomy of interest.

19. An ultrasound imaging system, comprising:
a console, including:
  transmit circuitry configured to generate an excitation electrical pulse that excites transducer elements of a probe to produce an ultrasound pressure field and configured to receive an echo signal generated in response to the ultrasound pressure field interacting with tissue;
  receive circuitry configured to convert the echo signal into an electrical signal;
  an echo processor configured to generate a live ultrasound image for each frame based on the electrical signal;
  a tracking processor configured to:
    obtain the live ultrasound image and volumetric image data that was previously generated by another imaging system, which was configured for three-dimensional imaging;
    extract, in real-time, an anatomical feature common to both the live ultrasound image and the previously generated volumetric image data from at least the live ultrasound image; and
    perform a single registration, in real-time, of the live ultrasound image with the volumetric image data based on the common anatomical feature extracted in real-time to create a fused image;
  wherein the tracking processor registers the live ultrasound image with the volumetric image data based on image registration transformation parameters, updates the image registration transformation parameters based on a latest result of the registration and an earlier result of the registration and applies a filter removing movement outliers,
and a display configured to display the fused image.

* * * * *